United States Patent [19]

Fujikawa et al.

[11] Patent Number: 4,639,444
[45] Date of Patent: Jan. 27, 1987

[54] 3,5-DIALKYL-4,6-DIARYL-TETRAHYDRO-2H-13,5-THIADIAZINE-2-THIONE DERIVATIVE, PROCESS FOR ITS PRODUCTION AND ANTIHYPERLIPIDEMIC AGENT CONTAINING IT

[75] Inventors: Yoshihiro Fujikawa, Funabashi; Mitsuaki Sakashita, Urawa; Nobutomo Tsuruzoe, Kuki, all of Japan

[73] Assignee: Nissan Chemical Industries Ltd., Tokyo, Japan

[21] Appl. No.: 800,025

[22] Filed: Nov. 20, 1985

[30] Foreign Application Priority Data

Nov. 30, 1984 [JP] Japan .................. 59-254921

[51] Int. Cl.$^4$ .................. C07D 285/34; C07D 407/10; A61K 31/54
[52] U.S. Cl. ........................................ 514/222; 544/8
[58] Field of Search .............................. 544/8; 514/222

[56] References Cited

U.S. PATENT DOCUMENTS 3,946,006 3/1976 Eggensperger et al. .............. 544/8

FOREIGN PATENT DOCUMENTS 118992 4/1976 German Democratic Rep. .
13045 8/1985 Japan .

OTHER PUBLICATIONS

Chemische Berichte, 100, 1967, p. 1614, R. Huigsgen et al.
Zeitschrift fuer Chemie, 14, 1974, p. 270, M. Augustin et al.
Die Pharmazie, 28, 1973, G. Würbach et al.

*Primary Examiner*—John M. Ford
*Attorney, Agent, or Firm*—Oblon, Fisher, Spivak, McClelland, & Maier

[57] ABSTRACT

A compound of the formula:

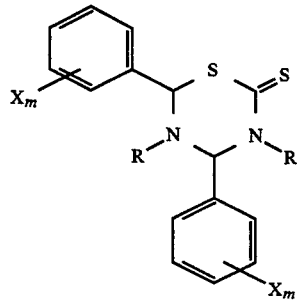

wherein R is methyl or ethyl, X is hydrogen (provided R is ethyl), lower alkyl, lower alkoxy, lower alkylthio, fluorine, bromine, phenoxy or substituted phenoxy, $X_m$ is methylenedioxy or —CH=CH—CH=CH—, and m is 1, 2 or 3.

31 Claims, No Drawings

3,5-DIALKYL-4,6-DIARYL-TETRAHYDRO-2H-1,3,5-THIADIAZINE-2-THIONE DERIVATIVE, PROCESS FOR ITS PRODUCTION AND ANTIHYPERLIPIDEMIC AGENT CONTAINING IT

The present invention relates to a novel 3,5-dialkyl-4,6-diaryl-tetrahydro-2H-1,3,5-thiadiazine-2-thione derivative, a process for its production and an antihyperlipidemic agent containing it.

Hyperlipidemia (hyperlipemia) is regarded as a major risk factor for the atherosclerosis. Heretofore, a number of antihyperlipidemic agents have been studied. Therapeutic agents in this field are likely to be used for an extended period of time in view of the nature of the diseases, and they are required to be highly safe. However, with respect to nicotinic acid and its derivatives, or clofibrate and its derivatives, which have been widely used as antihyperlipidemic agents, various side effects have been reported, and they can hardly be accepted as satisfactory therapeutic agents. For instance, with respect to nicotinic acid and its derivatives, it has been reported that they will bring about e.g. flashing or gastroenteric troubles. With respect to clofibrate and its derivatives, it is known that they will bring about e.g. myalgia or hepatic insufficiency, and they are likely to lead to gallstone formation. Further, it has been reported that clofibrate brings about hepatic carcinoma on animal experiments. [D. J. Svoboda and D. L. Azarnoff, Cancer Res., 39, 3419 (1979)]

Reflecting the progress in the recent years in the study of the lipid metabolism, particularly in the study of the functional mechanism of serum lipoprotein as a transporter of serum lipid, an attention about the effect of the drug has been drawn not only to the activity of the drug to reduce the lipid concentration in serum but also to the effect to the lipoprotein. Serum cholesterol constitutes the lipoprotein together with triglyceride, phospholipid and apoprotein. This lipoprotein is generally classified into Chylomicron, VLDL (very low density lipoprotein), LDL (low density lipoprotein) and HDL (high density lipoprotein) depending upon the difference in the specific gravity. Among them, Chylomicron, VLDL and LDL are believed to be the lipoproteins which induce atherosclerosis. Whereas, HDL is believed to have functions to transport cholesterol from peripheral blood vessels to a liver, to form a cholesterol ester or to contribute to the catabolism of triglyceride, and thus serves for the prevention and regression of the atherosclerosis. Accordingly, for an antihyperlipidemic agent to be developed, it is desired that such an agent has not only the function to reduce the total value of serum cholesterol, but also the functions to reduce LDL-cholesterol and to increase HDL-cholesterol.

The present inventors have conducted various researches for compounds having antihyperlipidemic effects, and finally found that novel 3,5-dialkyl-4,6-diaryl-tetrahydro-2H-1,3,5-thiadiazine-2-thione derivatives of the present invention have excellent antihyperlipidemic effects, and yet they have functions to reduce LDL-cholesterol and increase HDL-cholesterol. Further, they are highly safe with minimum toxicity. The present invention has been accomplished on the basis of these discoveries.

With respect to 3,5-dialkyl-4,6-diaryl-tetrahydro-2H-1,3,5-thiadiazine-2-thione derivatives of the present invention, only the syntheses of 3,5-dimethyl-4,6-diphenyl-tetrahydro-2H-1,3,5-thiadiazine-2-thione and 3,5-dimethyl-4,6-bis(p-chlorophenyl)-tetrahydro-2H-1,3,5-thiadiazine-2-thione are disclosed in Chemische Berichte, 100, 1602 (1967) or Zeitschrift fuer Chemie, 14, 270 (1974). No application of these compounds to medical or pharmaceutical agents has been known. Further, various derivatives having a basic structure of tetrahydro-2H-1,3,5-thiadiazine-2-thione without substitution at the 4- and 6-positions, have been synthesized and have been known as being useful as fungicides, insecticides or animal food additives (nutrients) [Arzneimittelforschung, 19, 1807 (1969)]. However, nothing has been known with respect to their antihyperlipidemic effects.

The novel 3,5-dialkyl-4,6-diaryl-tetrahydro-2H-1,3,5-thiadiazine-2-thiones having antihyperlipidemic effects according to the present invention are tetrahydro-2H-1,3,5-thiadiazine-2-thione compounds represented by the following formula I:

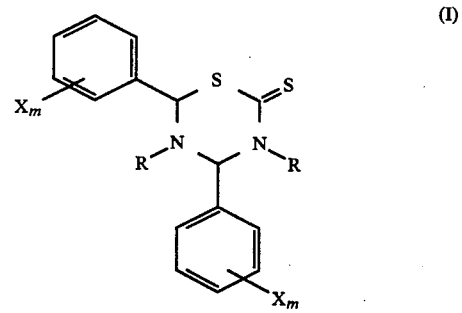

wherein R is methyl or ethyl, X is a hydrogen atom (provided R is ethyl), lower alkyl, lower alkyloxy, lower alkylthio, a bromine atom, a fluorine atom, phenoxy or substituted phenoxy, or $X_m$ is methylenedioxy or —CH=CH—CH=CH—, and m is 1, 2 or 3.

As the compounds of the present invention, the following compounds may be mentioned in addition to the compounds of the after-mentioned Examples:

3,5-diethyl-4,6-di-p-methoxyphenyl-tetrahydro-2H-1,3,5-thiadiazine-2-thione, 3,5-diethyl-4,6-di-m-methoxyphenyl-tetrahydro-2H-1,3,5-thiadiazine-2-thione, 3,5-diethyl-4,6-di-o-methoxyphenyl-tetrahydro-2H-1,3,5-thiadiazine-2-thione, 3,5-diethyl-4,6-di-p-methylphenyl-tetrahydro-2H-1,3,5-thiadiazine-2-thione, 3,5-diethyl-4,6-di-m-methylphenyl-tetrahydro-2H-1,3,5-thiadiazine-2-thione, 3,5-diethyl-4,6-di-p-ethoxyphenyl-tetrahydro-2H-1,3,5-thiadiazine-2-thione, 3,5-diethyl-4,6-di-p-fluorophenyl-tetrahydro-2H-1,3,5-thiadiazine-2-thione, 3,5-diethyl-4,6-di-p-isopropylphenyl-tetrahydro-2H-1,3,5-thiadiazine-2-thione, 3,5-diethyl-4,6-di-p-phenoxyphenyl-tetrahydro-2H-1,3,5-thiadiazine-2-thione, 3,5-diethyl-4,6-di-p-methylthiophenyl-tetrahydro-2H-1,3,5-thiadiazine-2-thione, 3,5-diethyl-4,6-bis-(2,4-dimethoxyphenyl)-tetrahydro-2H-1,3,5-thiadiazine-2-thione, 3,5-diethyl-4,6-bis-(3,4-methylenedioxyphenyl)-tetrahydro-2H-1,3,5-thiadiazine-2-thione, 3,5-diethyl-4,6-bis-(3,4,5-trimethoxyphenyl)-tetrahydro-2H-1,3,5-thiadiazine-2-thione, 3,5-diethyl-4,6-bis-(2,3-dimethoxyphenyl)-tetrahydro-2H-1,3,5-thiadiazine-2-thione,
3,5-diethyl-4,6-bis-(2,5-dimethylphenyl)-tetrahydro-2H-1,3,5-thiadiazine-2-thione,
3,5-diethyl-4,6-di-p-bromophenyl-tetrahydro-2H-1,3,5-thiadiazine-2-thione,
3,5-diethyl-4,6-di-m-phenoxyphenyl-tetrahydro-2H-1,3,5-thiadiazine-2-thione,
3,5-diethyl-4,6-di-(1-naphthyl)-tetrahydro-2H-1,3,5-thiadiazine-2-thione,
3,5-diethyl-4,6-di-(2-naphthyl)-tetrahydro-2H-1,3,5-thiadiazine-2-thione, and
3,5-diethyl-4,6-di-p-t-butylphenyl-tetrahydro-2H-1,3,5-thiadiazine-2-thione.

The overall process for the synthesis of tetrahydro-2H-1,3,5-thiadiazine-2-thiones of the formula I according to the present invention is represented by the following scheme.

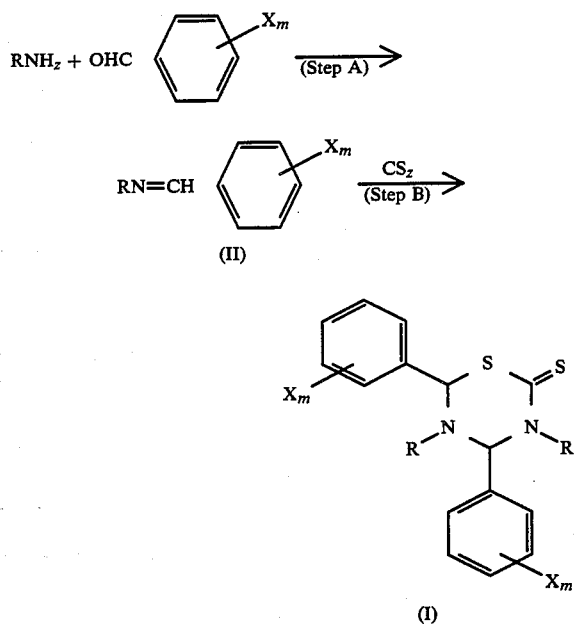

In the above reaction formulas, R, X and m are as defined above with respect to the formula I.

Step A is a process step of preparing a Shiff base of the formula II from a primary amine and a substituted benzaldehyde. This reaction is conducted in an aprotic solvent such as benzene or toluene at a temperature of from 0° to 3° C., and the water formed is distilled off by azeotropic distillation [Organic Synth., Col. Vol., 4, p 605]. Step B is a process step of a cyclization reaction of the Shiff base obtained by Step A with carbon disulfide. According to the conventional process [Chemishe Berichte, 100, 1602 (1967)], a great excess amount of carbon disulfide is used as a solvent, and the reaction system is left to stand still for a long period time or heated. And yet, according to this process, the substituted Shiff base does not substantially give the desired product in most cases.

The present inventors have conducted various studies on this reaction, and finally found that this reaction proceeds smoothly in such a water-free solvent as a dried lower alcohol such as dried methanol, dried ethanol or dried propanol, or dried acetonitrile, or a mixture thereof and the product crystallizes or precipitates therein. Further, they have found that it is sufficient for the reaction to use carbon disulfide in an amount of from 0.5 to 3 mols per mol of the Shiff base.

The compounds of the formula I of the present invention have remarkable antihyperlipidemic effects, and may be formulated into various suitable formulations depending upon the manner of the administration.

The pharmaceutical composition of the present invention comprises an effective amount of the compound of the formula I and a pharmaceutically acceptable carrier. The effective amount is usually at least 5% by weight, based on the total composition. As the pharmaceutically acceptable carrier, there may be mentioned a pharmaceutically acceptable binder such as a syrup, gum arabic, gelatin, sorbitol, tragacanth gum or polyvinyl pyrrolidone (molecula,r weight of e.g. about 25,000); an excipient such as lactose, sugar, corn starch, calcium phosphate, sorbitol or glycine; a lubricant such as magnesium stearate, talc, polyethylene glycol or silica; or a disintegrator such as potato starch. By properly selecting the carrier, the pharmaceutical composition of the present invention may be formulated into powders, granules, tablets or capsules. It is preferably administered orally. However, the manner of administration is not restricted to oral administration, and non-oral administration such as percutaneous administration, injection (through an intravenous, subcutaneous or intramuscular route) or rectal administration may be employed. For instance, it may be administered as a suppository as combined with oily base material such as cacao butter, polyethylene glycol, lanolin or fatty acid triglyceride.

The daily dose of the compound of the formula I is from 0.01 to 3.0 g, preferably from 0.1 to 2.0 g, for an adult. It is administered from once to three times per day. The dose may of course be varied depending upon the age, the weight or the condition of illness of the patient.

Now, the present invention will be described in further detail with reference to Test Examples for the antihyperlipidemic effects of the compounds of the formula I, Working Examples for the synthesis of the compounds of the formula I and Formulation Examples for the antihyperlipidemic agents. However, it should be understood that the present invention is by no means restricted to these specific Examples.

TEST 1

The antihyperlipidemic activity in emulsion-induced hyperlipidemic rats:

Male S. D. rats weighing 80–90 g (4 weeks old) were used. They were devided into groups of 5 to 6 rats each. The test compounds suspended in 0.5% CMC-Na(carboxymethyl cellulose sodium salt) were given to the rats in a daily dose of 4.0 ml/kg (i.e. 300 mg/kg of the test compounds) via stomach tube every 10:00 a.m. After 30 min., lipids emulsion having the following composition was orally given to the rats in an amount of 2.5 ml per rat.

| Composition of emulsion: | |
|---|---|
| Cholesterol | 22.5 g |
| Cholic acid sodium salt | 10.0 g |
| Sucrose | 90.0 g |
| Olive oil | 150.0 g |
| Water | X ml |
| Final volume | 300.0 ml |

During the experimental period of 3 days, the rats were fed on a standard commercial diet and water ad libitum. At the end of the period, the rats were fasted for 16 hours and then blood samples were obtained from inferior vena cava. The total cholesterol and HDL cholesterol were measured. The weight of the liver was measured. To the control group, only the aqueous CMC-Na solution and the lipids emulsion were given.

The fractionation of lipoproteins was conducted by a dextran sulfate-MgCl$_2$ precipitation method.

Cholesterol in serum was measured by means of a cholesterol measuring kit (Cholesterol C-Test Wako, manufactured by Wako Junyaku Co., Ltd.), and cholesterol in HDL was measured by means of NC Hi-Set, manufactured by Nippon Chemiphar Co., Ltd.

In the following description, cholesterol is referred to as "Chol".

Further, the reduction rate of Chol was calculated by the following equation.

$$\text{Reduction rate}(\%) = \frac{A - B}{A} \times 100$$

where A is the amount of serum Chol (mg/dl) of the control group, and B is the amount of serum Chol (mg/dl) of the group to which the therapeutic agent was administered.

Likewise, the increase rate of serum HDL-Chol was calculated by the following equation.

$$\text{Increase rate}(\%) = \frac{D - C}{C} \times 100$$

where C is the amount of serum HDL-Chol (mg/dl) of the control group, and D is the amount of serum HDL-Chol (mg/dl) of the group to which the therapeutic agent was administered.

The test results are shown in Tables 1 and 2.

TABLE 1

| | The effects of the compounds of the formula I for the reduction of serum Chol | | | |
|---|---|---|---|---|
| Compound No. | $X_m$ | R | Reduction rate of serum Chol. (%) | Increase rate of serum HDL-Chol. (%) |
| 1 | 4-Methoxy | Methyl | 42 | 53 |
| 2 | 3-Methoxy | Methyl | 41 | 25 |
| 3 | 2-Methoxy | Methyl | 32 | 33 |
| 4 | 4-Methyl | Methyl | 49 | 99 |
| 5 | 3-Methyl | Methyl | 44 | 52 |
| 6 | 2-Methyl | Methyl | 40 | 61 |
| 7 | 2-Ethoxy | Methyl | 37 | 14 |
| 8 | 4-Fluoro | Methyl | 26 | 37 |
| 9 | 4-i-Propyl | Methyl | 30 | 56 |
| 10 | 4-Phenoxy | Methyl | 53 | −23** |
| 11 | 4-Methylthio | Methyl | 13 | 53 |
| 12 | 2,4-Dimethoxy | Methyl | 31 | 46 |
| 13 | 3,4-Methylenedioxy | Methyl | 52 | 54 |
| 14 | 3,4,5-Trimethoxy | Methyl | 19 | 6 |

TABLE 1-continued

| | The effects of the compounds of the formula I for the reduction of serum Chol | | | |
|---|---|---|---|---|
| Compound No. | $X_m$ | R | Reduction rate of serum Chol. (%) | Increase rate of serum HDL-Chol. (%) |
| 15 | Not substituted | Ethyl | 45 | 31 |
| 16 | 2,3-Dimethoxy | Methyl | 34 | 44 |
| | Clofibrate* (Reference compound) | | 45 | −8* |

*Clofibrate

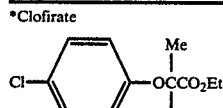

**Symbol "−" represents the reduction rate (%) of serum HDL-Chol.

TEST 2 ACUTE TOXICITY

The test compounds suspended in 0.5% CMC-Na were administered p.o. to male ddY mice. The acute toxicity was determined based on the mortality after seven days. In respect of the Compound Nos. 1, 2, 3, 4, 6, 7, 10, 12 and 13 of the present invention, the mortality was 0% even at a dose of as high as 4000 mg/kg by oral administration.

EXAMPLE 1

3,5-Dimethyl-4,6-di(p-methoxyphenyl)-tetrahydro-2H-1,3,5-thiadiazine-2-thione (compound No.1)

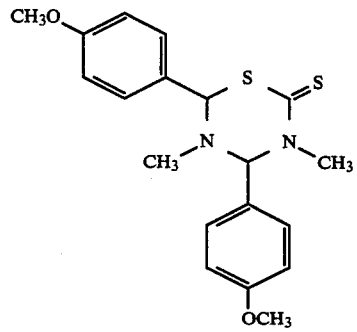

To a solution obtained by dissolving 7.45 g (0.05 mol) of N-p-methoxyphenylmethylidene-methylamine in 30 ml of dried ethanol, 3.8 g (0.05 mol) of carbon disulfide was dropwise added. The mixture was stirred at room temperature for 2 hours, and then left to stand still for about 2 days, whereupon the precipitated crystals were filtered off, and recrystallized from acetonitrile.

Yield: 5.0 g (53.5%), white prism crystals,

Melting point: 124°–126° C.

Compound Nos. 2 to 23 were synthesized in the same manner as in Example 1. The yields, the melting points and the main values of the pmr spectrum of these compounds are shown in Table 2.

TABLE 2

| | Examples of the synthesis of the compounds of the formula I | | | | | | |
|---|---|---|---|---|---|---|---|
| Compound No. | $X_m$ | R | Yield (After recrystallization) (°C.) | Melting point (°C.) | pmr: δ value (ppm) in CDCl$_3$ | | |
| | | | | | N—C$\underline{H}_3$* | | $\underline{H}$ at the 4- and 6-positions of the thiadiazine ring* |
| 1 | 4-Methoxyphenyl | Methyl | 53.5 | 124–126 | 2.45 | 3.60 | 5.46 5.60 |
| 2 | 3-Methoxyphenyl | Methyl | 56.8 | 123–125 | 2.50 | 3.62 | 5.47 5.66 |
| 3 | 2-Methoxyphenyl | Methyl | 61.5 | 160–161 | 2.54 | 3.38 | 5.72 6.29 |
| 4 | 4-Methylphenyl | Methyl | 58.0 | 138–139.5 | 2.46 | 3.60 | 5.47 5.63 |

TABLE 2-continued

Examples of the synthesis of the compounds of the formula I

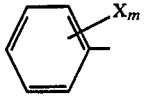

| Compound No. | | R | Yield (After recrystallization) (°C.) | Melting point (°C.) | pmr: δ value (ppm) in CDCl$_3$ N—CH$_3$* | | H at the 4- and 6-positions of the thiadiazine ring* | |
|---|---|---|---|---|---|---|---|---|
| 5 | 3-Methylphenyl | Methyl | 59.6 | 151–153 | 2.48 | 3.60 | 5.45 | 5.66 |
| 6 | 2-Methylphenyl | Methyl | 64.5 | 183 | 2.49 | 3.52 | 5.46 | 5.93 |
| 7 | 2-Ethoxyphenyl | Methyl | 68.5 | 159–161.5 | 2.57 | 3.46 | 5.75 | 6.47 |
| 8 | 4-Fluorophenyl | Methyl | 34.9 | 161–165 | 2.45 | 3.60 | 5.48 | 5.56 |
| 9 | 4-Isopropylphenyl | Methyl | 36.8 | 149–151 | 2.49 | 3.61 | 5.48 | 5.65 |
| 10 | 4-Phenoxyphenyl | Methyl | 53.7 | 165–168 | 2.48 | 3.61 | 5.48 | 5.65 |
| 11 | 4-Methylthiophenyl | Methyl | 53.4 | 132.5–133.5 | 2.45 | 3.60 | 5.46 | 5.59 |
| 12 | 2,4-Dimethoxyphenyl | Methyl | 56.8 | 105–111 | 2.50 | 3.48 | 5.63 | 6.21 |
| 13 | 3,4-Methylenedioxyphenyl | Methyl | 60.9 | 154–155 | 2.44 | 3.59 | 5.38 | 5.59 |
| 14 | 3,4,5-Trimethoxyphenyl | Methyl | 33.6 | 177–178 | 2.50 | 3.63 | 5.44 | 5.62 |
| 15 | Phenyl | Ethyl | 14.8 | 164 | (N—CH$_2$—CH$_3$)** 1.15(t) 1.34(t) | | 5.25(q)*** | 5.65 |
| 16 | 2,3-Dimethoxyphenyl | Methyl | 64.4 | 150–153.5 | 2.59 | 3.48 | 5.79 | 6.30 |
| 17 | 4-Bromophenyl | Methyl | 30.5 | 174–175 | 2.45 | 3.59 | 5.45 | 5.53 |
| 18 | 2,5-Dimethylphenyl | Methyl | 58.0 | 198–200.5 | 2.47 | 3.52 | 5.42 | 5.91 |
| 19 | 3-Phenoxyphenyl | Methyl | 42.1 | 150–153 | 2.46 | 3.60 | 5.43 | 5.66 |
| 20 | 1-Naphthyl | Methyl | 45.6 | 168.5–173 | 2.57 | 3.68 | 6.19 | 6.38 |
| 21 | 2-Naphthyl | Methyl | 23.0 | 192–193 | 2.54 | 3.72 | 5.70 | 5.81 |
| 22 | 4-t-Butylphenyl | Methyl | 33.6 | 177–178 | 2.50 | 3.63 | 5.44 | 5.62 |
| 23 | 2-Methylphenyl | Ethyl | 21.1 | 144–147 | (N—CH$_2$—CH$_3$)** 1.01(t) 1.33(t) | | 5.66 | 5.91 |

*Singlet unless otherwise specified
**t: Triplet
***q: Quartet

Now, there will be given Examples for formulations containing antihyperlipidemic compounds of the present invention.

Formulation Example 1: Tablets

| Composition (4,000 tablets) | |
|---|---|
| Compound No. 1 | 500 (g) |
| Potato starch | 334 |
| Carboxymethyl cellulose | 87.5 |
| Polyvinyl alcohol | 61 |
| Magnesium stearate | 17.5 |
| | 1,000 |

The above ingredients in the respective amounts were introduced into a twin shell mixer and uniformly mixed. This powder mixture was tableted by a direct compression method to obtain tablets having a weight of 250 mg per tablet.

Formulation Example 2: Capsules

| Composition (1,000 capsules) | |
|---|---|
| Compound No. 2 | 250 (g) |
| Patato starch | 40 |
| Magnesium stearate | 10 |
| | 300 |

The above ingredients in the respective amounts were introduced into a twin shell mixer and uniformly mixed. This pwder mixture was packed in hard gelatin capsules in an amount of 300 mg per capsule.

Formulation Example 3: Powder

| Composition: | |
|---|---|
| Compound No. 3 | 200 (g) |
| Lactose | 800 |
| | 1,000 |

The above ingredients in the respective amounts were introduced into a twin shell mixer and uniformly mixed.

Formulation Example 4: Granules

| Composition (1,000 packages) | |
|---|---|
| Compound No. 4 | 100 (g) |
| Silicic anhydride | 80 |
| Crystalline cellulose | 180 |
| Lactose | 130 |
| Magnesium stearate | 10 |
| | 500 |

The above ingredients in the respective amounts were uniformly mixed, then granulated and packaged in an amount of 500 mg per package.

Formulation Example 4: Suppository

| Composition (1,000 pcs) | |
|---|---|
| Compound No. 5 | 200 (g) |
| Cacao butter | 1,000 |
| | 1,200 |

The above ingredients in the respective amounts were uniformly melted at 38° C., and poured into a casting mold for suppository which was preliminarily cooled. The weight per piece of suppository was 1.2 g.

We claim:

1. A compound of the formula:

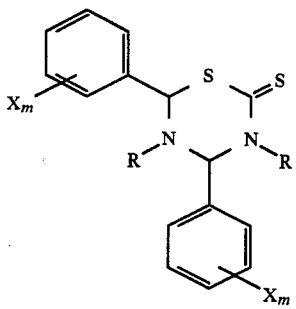

wherein R is methyl or ethyl, m is 1, 2 or 3, X is independently selected from hydrogen, a lower alkyl, lower alkoxy, lower alkylthio, fluorine, bromine, phenoxy or substituted phenoxy, with the proviso that when X is hydrogen, R is ethyl and 2X taken together is methylenedioxy or —CH=CH—CH=CH—, and with the further proviso that the substituents on the substituted phenoxy are selected from the group consisting of a lower alkyl, lower alkoxy, lower alkylthio, fluorine and bromine.

2. The compound of claim 1, wherein X is hydrogen, $C_{1-4}$ alkyl, $C_{1-4}$ alkoxy, $C_{1-4}$ alkylthio, fluorine, bromine or phenoxy, or 2X taken together is methylenedioxy, with the proviso that when X is hydrogen, R is ethyl.

3. The compound of claim 1, wherein X is hydrogen, methyl, isopropyl, tertiary butyl, methoxy, ethoxy, methylthio, fluorine, bromine or phenoxy, or 2X taken together is methylenedioxy, with the proviso that when X is hydrogen, R is ethyl.

4. The compound of claim 1, wherein R is methyl, X is $C_{1-4}$ alkyl, $C_{1-4}$ alkoxy, $C_{1-4}$ alkylthio, fluorine, bromine or phenoxy, or 2X taken together is methylenedioxy.

5. The compound of claim 1, wherein R is ethyl, and X is hydrogen, methyl or ethyl.

6. The compound of claim 1, wherein R is methyl, X is methyl, isopropyl, tertiary butyl, methoxy, ethoxy, methylthio, fluorine, bromine or phenoxy, or 2X taken together is methylenedioxy.

7. A process for producing a compound of the formula:

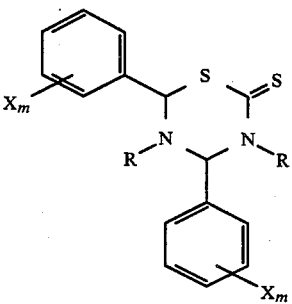

wherein R is methyl or ethyl, m is 1, 2 or 3, X is independently selected from hydrogen, a lower alkyl, lower alkoxy, lower alkylthio, fluorine, bromine, phenoxy or substituted phenoxy, with the proviso that when X is hydrogen, R is ethyl and 2X taken together is methylenedioxy or —CH=CH—CH=CH—, and with the further proviso that the substituents on the substituted phenoxy are selected from the group consisting of a lower alkyl, lower alkoxy, lower alkylthio, fluorine and bromine, which comprises reacting a compound of the formula:

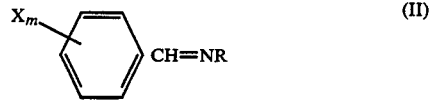

wherein X, R and m are as defined above, with carbon disulfide in an anhydrous solvent selected from the group consisting of dried $C_1$-$C_3$ alcohol, dried acetonitrile and a mixture thereof where carbon disulfide is added in an amount of from 0.5 to 3 moles per mole of the compound of formula.

8. An atherosclerosis reducing pharmaceutical composition comprising an atherosclerosis reducing effective amount of a compound of claim 1, and a pharmaceutically acceptable carrier.

9. An antihyperlipidemic pharmaceutical composition comprising an antihyperlipidemically effective amount of a compound of claim 1, and a pharmaceutically acceptable carrier.

10. A pharmaceutical composition for raising the ratio of high density lipoprotein chlesterol to total cholesterol in serum, comprising a ratio raising effective amount of a compound of claim 1 and a pharmaceutically acceptable carrier.

11. A method of reducing the incidence or severity of atherosclerosis in a subject comprising administering to said subject an amount effective to reduce the incidence or severity of atherosclerosis of a compound of claim 1.

12. A method of treating hyperlipidemia in a subject comprising administering to said subject an antihyperlipidemically effective amount of a compound of claim 1.

13. A method of raising the ratio of high density lipoprotein cholesteriol in serum in a subject in need of such raising of ratio, comprising administering to said subject a ratio raising effective amount of a compound of claim 1.

14. The compound of claim 1, wherein R is methyl, X is methyl, isopropyl, methoxy, ethoxy, methylthio, fluorine or bromine, or 2X taken together is methylenedioxy.

15. The compound of claim 1, wherein R is methyl, m is 1, X is $C_{1-4}$ alkyl, $C_{1-4}$ alkoxy, $C_{1-4}$ alkylthio, fluorine, bromine, phenoxy or substituted phenoxy with the proviso that the substituents on the substituted phenoxy are selected from the group consisting of a lower alkyl, lower alkoxy, lower alkylthio, fluorine or bromine.

16. The compound of claim 1, wherein R is methyl, m is 2, X is methyl, isopropyl, methoxy, ethoxy, methylthio, fluorine or bromine, or 2X taken together is methylenedioxy or —CH=CH—CH=CH—.

17. The compound of claim 1, where R is methyl, m=3, X is methyl, methoxy, ethoxy, methylthio or fluorine, or 2X taken together is methylenedioxy.

18. 3,5-dimethyl-4,6-di-p-methoxyphenyl-tetrahydro-2H-1,3,5-thiadiazine-2-thione, according to claim 1.

19. 3,5-dimethyl-4,6-di-m-methoxyphenyl-tetrahydro-2H-1,3,5-thiadiazine-2-thione, according to claim 1.

20. 3,5-dimethyl-4,6-di-o-methoxyphenyl-tetrahydro-2H-1,3,5-thiadiazine-2-thione, according to claim 1.

21. 3,5-dimethyl-4,6-di-p-methylphenyl-tetrahydro-2H-1,3,5-thiadiazine-2-thione according to claim 1.

22. 3,5-dimethyl-4,6-di-m-methylphenyl-tetrahydro-2H,3,5-thiadiazine-2-thione, according to claim 1.

23. 3,5-dimethyl-4,6-di-p-ethoxyphenyl-tetrahydro-2H-1,3,5-thiadiazine-2-thione, according to claim 1.

24. 3,5-dimethyl-4,6-di-p-fluorophenyl-tetrahydro-2H-1,3,5-thiadiazine-2-thione, according to claim 1.

25. 3,5-dimethyl-4,6-p-isopropylphenyl-tetrahydro-2H-1,3,5-thiadiazine-2-thione, according to claim 1.

26. 3,5-dimethyl-4,6-di-p-phenoxyphenyl-tetrahydro-2H-1,3,5-thiadiazine-2-thione, according to claim 1.

27. 3,5-dimethyl-4,6-di-p-methylthiophenyl-tetrahydro-2H-1,3,5-thiadiazine-2-thione, according to claim 1.

28. 3,5-dimethyl-4,6-bis-(2,4-dimethoxyphenyl)-tetrahydro-2H-1,3,5-thiadiazine-2-thione, according to claim 1.

29. 3,5-dimethyl-4,6-bis-(3,4-methylenedioxyphenyl)-tetrahydro-2H-1,3,5-thiadiazine-2-thione, according to claim 1.

30. 3,5-dimethyl-4,6-bis-(3,4,5-trimethoxyphenyl)-tetrahydro-2H-1,3,5-thiadiazine-2-thione, according to claim 1.

31. 3,5-dimethyl-4,6-bis-(2,3-dimethoxyphenyl)-tetrahydro-2H-1,3,5-thiadiazine-2-thione, according to claim 1.

* * * * *

UNITED STATES PATENT AND TRADEMARK OFFICE
CERTIFICATE OF CORRECTION

PATENT NO. : 4,639,444  
DATED : JANUARY 27, 1987  
INVENTOR(S) : YOSHIHIRO FUJIKAWA ET AL

Page 1 of 2

It is certified that error appears in the above-identified patent and that said Letters Patent is hereby corrected as shown below:

In the title, line 2, delete "13, 5" and insert --1, 3, 5--.

Column 3, line 55, delete "Chemishe" and insert --Chemische--.

Column 3, line 58, delete "period time" and insert --period of time--.

Column 4, lines 14-15, delete "polyvinyl pyrrolidone (molecula,r" and insert --polyvinylpyrrolidone (molecular--.

Column 4, line 52, delete "devided" and insert --divided--.

Column 6, line 9, delete "-8*" and insert -- -8**--.

Column 6, line 11, delete "Clofirate" and insert --Clofibrate--.

Columns 7 and 8, in table 2, heading, delete "Examples of the synthesis" and insert --Examples for the synthesis--.

UNITED STATES PATENT AND TRADEMARK OFFICE
CERTIFICATE OF CORRECTION

PATENT NO. : 4,639,444

DATED : JANUARY 27, 1987

INVENTOR(S) : YOSHIHIRO FUJIKAWA ET AL

It is certified that error appears in the above-identified patent and that said Letters Patent is hereby corrected as shown below:

Column 7, line 54, delete "Patato" and insert --Potato--.

Column 7, line 60, delete "pwder" and insert --powder--.

In claim 10, line 2, delete "chlesterol" and insert --cholesterol--.

In claim 13, line 2, delete "cholesteriol" and insert --cholesterol--.

In claim 17, line 1, delete "where" and insert --wherein--.

In claim 21, line 2, delete "thione according" and insert --thione, according--.

In claim 22, line 2, delete "2H,3,5" and insert --2H-1,3,5--.

In claim 25, line 1, delete "4,6-p" and insert --4,6-di-p--.

Signed and Sealed this

Thirty-first Day of May, 1988

Attest:

DONALD J. QUIGG

Attesting Officer

Commissioner of Patents and Trademarks